(12) United States Patent
Koo et al.

(10) Patent No.: US 7,709,247 B2
(45) Date of Patent: May 4, 2010

(54) METHODS AND SYSTEMS FOR DETECTING BIOMOLECULAR BINDING USING TERAHERTZ RADIATION

(75) Inventors: Tae-Woong Koo, Cupertino, CA (US);
Andrew Berlin, San Jose, CA (US);
Ken Salsman, Pleasanton, CA (US);
Brian Ostrovsky, Portland, OR (US)

(73) Assignee: Intel Corporation, Santa Clara, CA (US)

(*) Notice: Subject to any disclaimer, the term of this patent is extended or adjusted under 35 U.S.C. 154(b) by 0 days.

(21) Appl. No.: 10/911,441

(22) Filed: Aug. 4, 2004

(65) Prior Publication Data

US 2006/0029941 A1   Feb. 9, 2006

(51) Int. Cl.
*C12M 1/34* (2006.01)
*C12M 3/00* (2006.01)

(52) U.S. Cl. .................. 435/287.1; 436/524; 436/528; 435/7.1; 435/283.1; 435/287.2; 435/288.7; 422/50; 422/61; 422/68.1; 422/82.11; 422/82.09; 422/82.05

(58) Field of Classification Search .............. 435/4, 435/7.1, 283.1, 287.1, 287.2, 288.7; 436/518, 436/524, 528; 422/50, 61, 68.1, 82.11, 82.09, 422/82.05
See application file for complete search history.

(56) References Cited

U.S. PATENT DOCUMENTS

| | | | |
|---|---|---|---|
| 4,777,129 A * | 10/1988 | Dattagupta et al. .............. 435/6 |
| 5,081,012 A * | 1/1992 | Flanagan et al. .............. 435/7.9 |
| 5,206,347 A | 4/1993 | Ruoslahti et al. |
| 5,264,563 A | 11/1993 | Huse |
| 5,401,511 A | 3/1995 | Margalit |
| 5,603,872 A | 2/1997 | Margalit |
| 5,622,699 A | 4/1997 | Ruoslahti |
| 6,263,286 B1 | 7/2001 | Gilmanshin et al. |
| 6,483,096 B1 * | 11/2002 | Kunz et al. ............. 250/214 R |
| 6,511,854 B1 * | 1/2003 | Asanov et al. ............. 436/518 |
| 2004/0058339 A1 * | 3/2004 | Nagel et al. ..................... 435/6 |
| 2004/0227089 A1 * | 11/2004 | Kolodzey et al. ........ 250/341.8 |
| 2004/0248144 A1 * | 12/2004 | Mir ............................... 435/6 |
| 2005/0242287 A1 * | 11/2005 | Hakimi .................. 250/363.09 |
| 2006/0045807 A1 * | 3/2006 | Zhang et al. ............. 422/82.05 |
| 2006/0049356 A1 * | 3/2006 | Shen et al. ............... 250/341.1 |

FOREIGN PATENT DOCUMENTS

WO   WO 89/10977   11/1989

OTHER PUBLICATIONS

Brucherseifer et al., Dec. 2000, Label-free probing of the binding state of DNA by time-domain terahertz sensing, Applied Physics Letters, vol. 77, No. 24, pp. 4049-4051.*

(Continued)

*Primary Examiner*—Melanie Yu
(74) *Attorney, Agent, or Firm*—Pillsbury Winthrop Shaw Pittman LLP

(57) ABSTRACT

Provided herein are methods and systems for detecting biomolecular binding events using gigahertz or terahertz radiation. The methods and systems use low-energy spectroscopy to detect biomolecular binding events between molecules in an aqueous solution. The detected biomolecular binding events include, for example, nucleic acid hybridizations, antibody/antigen binding, and receptor/ligand binding.

16 Claims, 6 Drawing Sheets

OTHER PUBLICATIONS

Mickan et al. 2002, Label-free bioaffinity detection using terahertz technology, Phys. Med. Biol., vol. 47, pp. 3789-3795.*

Blondelle et al. (1995). "Soluble combinatorial libraries of organic, peptidomimetic and peptide diversities," *Trends in Analytical Chemistry* 14(2):83-92.

Borrebeck. (1995). *Antibody Engineering: 2nd Edition*. Oxford University Press, New York, NY.

Craighead. (2000). "Nanelectromechanical Systems," *Science* 290:1532-1535.

deKruif et al. (1996). "Biosythetically lipid-modified human scFv fragments from phage display libraries as targeting molecules for immunoliposomes," *FEBS Letters* 399:232-236.

Ding et al. (1995). "Synthesis and biological activity of oligosaccharide libraries," *Glycoimmunology* (*Advances in Experimental Medicine and Biology*). Eds. Alavi, Azita and Axford, John S. Plenium Press: New York, NY. pp. 261-269.

Ecker and Crooke. (1995). "Combinatorial Drug Discovery: Which Methods Will Produce the Greatest Value?," *Bio/Technology* 13:351-360.

Gordon et al. (1994). "Applications of combinatorial technologies to drug discover. 2. Combinatorial organic synthesis, library screening strategies, and future directions," *Journal of Medicinal Chemistry* 37(10):1385-1401.

Green et al. (1992). "Production of Polyclonal Antisera," *Immunochemical Protocols*. Ed. Manson, Margaret M. Humana press: Totowa, NJ. pp. 1-5.

Harlow and Lane. (1988). *Antibodies: A labratory manual*, Cold Springs Harbor Laboratory Press, Cold Springs Harbor, NY.

Hilyard et al. (1992). "Protein engineering of antibody combining sites," *Protein Engineering: A Practical Approach*, eds. Rees, Anthony et al. IRL Press, New York, NY. pp. 253-275.

Holmstrom et al. (1993). "A highly sensitive and fast nonradioactive method for detection of polymerase chain reaction products," *Analytical Biochemistry* 209:278-283.

Huse et al. (Dec. 8, 1989). "Generation of a Large Combinatorial Library of the Immunoglobulin Repertoire in Phage Lambda," *Science* 246:1275-1281.

Karaoglu et al. (1995). "Functional characterization of Ost3p. Loss of the 34-kD subunit of the *Saccharomyces cerevisiae* Oligosaccharyltransferase results in biased underglycosylation of acceptor substrates," *The Journal of Cell Biology* 130:567-577.

Lai et al. (1998). "A photoconductive, miniature terahertz source," *Applied Physics Letters* 72(24):3100-3102.

Liang et al. (1996). "Parallel Synthesis and Screening of a Solid Phase Carbohydrate Library," *Science* 274:1520-1522.

Markland et al. (1991). "Design, construction and function of a multicopy display vector using fusions to the major coat protein of bacteriophage M13," *Gene* 109:13-19.

Scott and Smith. (1992). "Searching for Peptide Ligands with an Epitope Library," *Science* 249:386-390.

Voldman et al. (1999). "Microfabrication in biology and medicine," *Annual Review of Biomedical Engineering* 1:401-425.

Ward et al. (1989). "Binding activities of a repertoire of single immunoglobulin variable domains secreted from *Escherichia coli*" *Nature* 341:544-546.

Williamson et al. (2003). "Determination of gas temperature in an open-air atmospheric pressure plasma torch from resolved plasma emission," *Journal of Applied Physics* 93(4): 1893-1898.

Winter and Harris. (1993). "Humanized antibodies," *Immunology Today* 14:243-246.

Xing and Liu. (1995). "Novel voltage-tunable far-infrared and terahertz detector based on a quantum ballistic channel," *Semiconductor Science Technology* 10:1139-1144.

York et al. (1996). "The structures of arabinoxyloglucans produced by solanaceous plants," *Carbohydrate Research* 285:99-128.

Knab et al. (2004). "Protein-ligand binding detected by terahertz spectroscopy," *Biophysical Journal* 86(1):84a.

* cited by examiner

METHODS AND SYSTEMS FOR DETECTING BIOMOLECULAR BINDING USING TERAHERTZ RADIATION

BACKGROUND OF THE INVENTION

1. Field of the Invention

The invention relates generally to detecting a biomolecular binding event and more particularly to detecting such events using spectroscopy.

2. Background Information

Many current methods for detecting disease or the risk of developing a disease rely on detection of one or more biomolecular interactions between a target molecule in the biological sample and a detectable probe molecule. The probe molecule is typically detectable because it is bound to a detectable label. For example, infection in a subject caused by an infectious agent, such as a virus, can be detected by detecting binding of a labeled antibody probe to a viral protein. A plethora of bioassays have been developed based on this general concept.

Some more recent methods for detecting disease rely on the detection or determination of a nucleic acid sequence in a test sample. Sequence-selective detection of nucleic acid molecules has become increasingly important as scientists unravel the genetic basis of disease and use this new information to improve medical diagnosis and treatment. Nucleic acid hybridization assays are specific biomolecular binding assays that are commonly used to detect the presence of specific nucleic acid sequences in a sample. For example, an infectious agent can be detected by detecting hybridization of a labeled nucleic acid probe to a nucleic acid of the virus. Alternatively, the method can base disease detection on detection or determination of all or a part of the patient's own nucleic acid sequences. For example, a patient's risk for developing a disease can be determined by detection of a genetic mutation.

Like other methods that detect biomolecular interactions, nucleic acid hybridization assays typically utilize a labeled probe. Traditionally, radioisotopes have been used as labels. More recently, fluorescent, chemiluminescent and bioactive reporter groups have been used. However, the inclusion of labels in an assay often makes it more expensive and complicated, and increases the background signal of the assay.

Hybridization assays can be used not only to detect the presence of a nucleic acid molecule, but determine the sequence of the nucleic acid molecule as well. Traditional approaches for sequence determination utilize the synthesis of labeled nucleic acids that are terminated at one of the four nucleotides. However, these methods are relatively slow and expensive. More recently, methods have been developed that entail synthesizing oligonucleotides on a glass support and effecting hybridization with radioactively or fluorescently-labeled test DNA, and reconstructing nucleotide sequence on the basis of data analysis (E. Southern et al., PCT/GB 89/00460, 1989). A device for carrying out such methods includes a supporting film or glass plate and an array of nucleotides covalently attached to the surface thereof. The array includes a set of oligonucleotides of desired length that are capable of taking part in a hybridization reaction.

The sequencing-by-hybridization method discussed above, although providing a less-expensive method with higher-throughput, has certain disadvantages. For example, it typically requires labeling of sample or probe nucleic acids. As discussed above, this increases the cost and complexity of the method and increases background values, thereby decreasing sensitivity. Furthermore, inclusion and detection of labels lowers the throughput of the assay.

In an attempt to determine nucleic acid sequences information more efficiently, ultraviolet/visible/near-infrared spectroscopy has been used to directly detect hybridization. Although this type of spectroscopy has successfully detected events for smaller molecules (e.g., $CO_2$), it failed to provide the desired level of efficiency and accuracy for biomolecules, which tend to be larger. The frequency shift in the vibration spectrum that is experienced by larger biomolecules (e.g., DNA) upon binding is too small to be accurately and efficiently detected by UV/visible/near-infrared spectroscopy. Furthermore, the UV/visible/near-infrared radiation causes the molecules to fluoresce, creating background noise that interferes with spectrum signals. Further, the method requires multiple gratings of strong dispersion to resolve the small frequency change, making the optical instrument too bulky for convenient use.

DETAILED DESCRIPTION OF THE INVENTION

Figure 1:
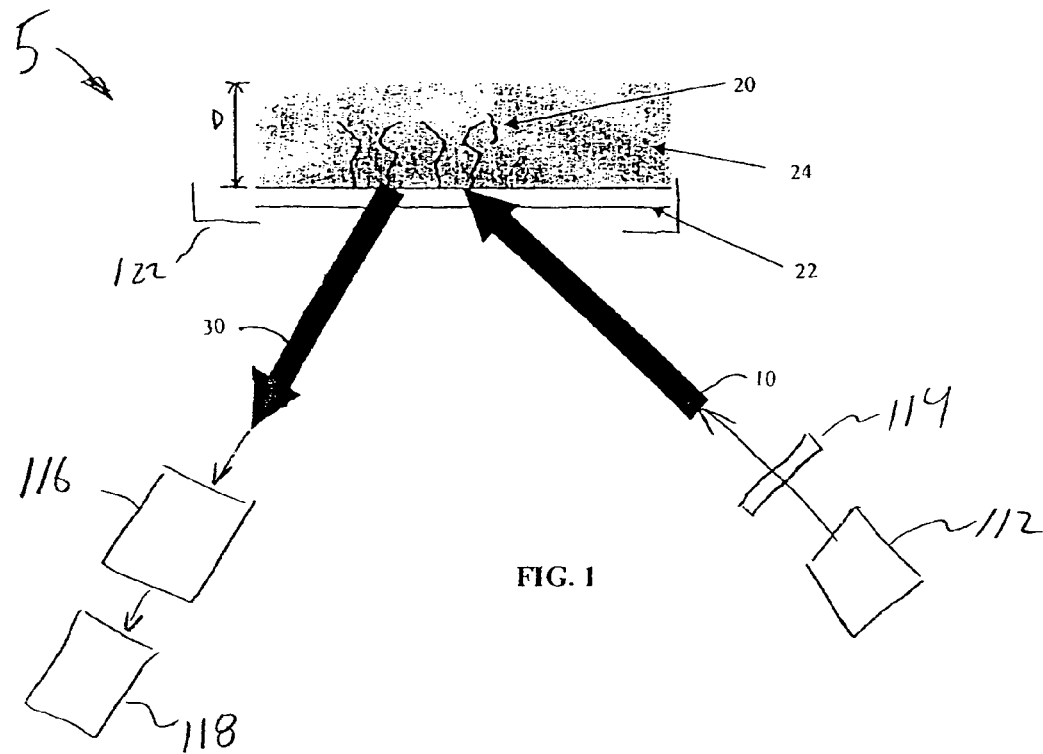
FIG. 1 is an illustration of an embodiment of a system whereby terahertz radiation 10 impinges a nucleic acid molecule 20 immobilized on a transparent substrate 22. The excitation and signal collection can be performed, for example, through the substrate.

The methods and systems provided herein are based on the use of terahertz radiation to detect biomolecular binding events. The use of one terahertz radiation to detect molecular binding events provides numerous advantages over currently available detection methods. First, because labels are not necessary and because low-energy terahertz radiation does not cause fluorescence, background levels are reduced. Second, by using low-energy terahertz radiation instead of ultraviolet/visible/near-infrared radiation, only one grating is needed to obtain a meaningful spectroscopy result. Due to the fact that multiple gratings are not necessary, the instrument can become more compact and less expensive. Third, the use of terahertz radiation allows the biomolecular signature of the sample to be obtained in a dormant state, without exciting molecules of the sample to an unnecessarily high energy level, and possibly altering the molecules or their interactions.

The invention is founded, at least in part, on the discovery that terahertz/gigahertz radiation spectroscopy allows efficient and accurate monitoring of biomolecular binding events without the inconveniences and high backgrounds associated with the currently available methods. The terahertz/gigahertz radiation instrument of the invention specifically excites the molecules in the low frequency vibrational bands, thereby significantly reducing background noise in the signals and, at the same time, eliminating the need for multiple gratings.

In one embodiment, a method includes preparing a sample including a first molecule and a second molecule, directing an input radiation at the sample, whereby the input radiation is gigahertz or terahertz radiation, and detecting exit radiation traveling from the sample, is provided. A shift in vibrational frequency or a change in intensity level of the exit radiation compared to exit radiation detected from a first molecule not bound to the second molecule, is indicative of a biomolecular interaction. At least one of the molecules is typically a biomolecule. In an illustrative example, the biomolecular binding event is hybridization of a first nucleic acid molecule to a second nucleic acid molecule.

In another embodiment, a method of detecting a biomolecular binding event by preparing a sample including a first molecule and a second molecule, directing an input radiation at the sample, is provided. The input radiation excites the sample without causing fluorescence. The exit radiation traveling from the sample is examined for a shift in vibrational frequency, wherein a shift in vibrational frequency or a change in intensity level of the exit radiation compared to exit radiation detected from a first molecule not bound to the second molecule, is indicative of a biomolecular interaction.

In another embodiment, an apparatus for detecting a biomolecular binding event is provided. The apparatus includes a terahertz light source or terahertz radiation source positioned to aim an input radiation toward the sample and a detector for receiving an exit radiation reflecting from the sample. A processor is also provided to receive the data from the detector and analyze the data. In some embodiments, the light source, detector and processor are located in a housing. A filter may also be positioned between the light source and the sample. An optional sample holder may also be provided.

In yet another embodiment, a system for detecting a biomolecular binding event is provided. The system includes a sample containing a first molecule and a second molecule, a gigahertz or terahertz radiation source positioned to aim an input radiation toward the sample, and a detector for receiving an exit radiation reflecting from the sample. The system detects exit radiation traveling from the sample upon excitation by the input radiation, wherein a shift in vibrational frequency or a change in intensity level of the exit radiation compared to exit radiation detected from a first molecule not bound to the second molecule, is indicative of a biomolecular interaction.

In methods provided herein, the first molecule is typically a biomolecule. The second molecule can also be a biomolecule. For example, a second molecule, which is typically a molecule to be detected by the method, is a virus, bacteria, or an analyte, such as, but not limited to, a protein, a nucleic acid, a peptide, a polysaccharide, or a fatty acid.

As used herein, "a" or "an" may mean one or more than one of an item.

"Nucleic acid" encompasses DNA, RNA, single-stranded, double-stranded or triple stranded and any chemical modifications thereof. Virtually any modification of the nucleic acid is contemplated. As used herein, a single stranded nucleic acid may be denoted by the prefix "ss", a double stranded nucleic acid by the prefix "ds", and a triple stranded nucleic acid by the prefix "ts." For methods provided herein, a biomolecule in illustrative examples, is a single-stranded nucleic acid molecule. Nucleic acids in the methods provided herein include viral, bacterial, and animal, for example mammalian, or, more specifically, human nucleic acids.

A "nucleic acid" may be of almost any length, for example from 10, 20, 30, 40, 50, 60, 75, 100, 125, 150, 175, 200, 225, 250, 275, 300, 400, 500, 600, 700, 800, 900, 1000, 1500, 2000, 2500, 3000, 3500, 4000, 4500, 5000, 6000, 7000, 8000, 9000, 10,000, 15,000, 20,000, 30,000, 40,000, 50,000, 75,000, 100,000, 150,000, 200,000, 500,000, 1,000,000, 1,500,000, 2,000,000, 5,000,000 or even more bases in length, up to a full-length chromosomal DNA molecule.

Nucleic acid molecules to be analyzed can be prepared by any technique known in the art. In certain embodiments, the nucleic acids are naturally occurring DNA or RNA molecules. Virtually any naturally occurring nucleic acid may be prepared and sequenced by the disclosed methods including, without limit, chromosomal, mitochondrial and chloroplast DNA and ribosomal, transfer, heterogeneous nuclear and messenger RNA.

A "biological sample" includes, for example, urine, blood, plasma, serum, saliva, semen, stool, sputum, cerebral spinal fluid, tears, mucus, ejaculate, cerebrospinal fluid, pleural fluid, ascites fluid, or a biopsy sample.

In certain aspects, the biological sample is from a mammalian subject, for example a human subject. The biological sample can be virtually any biological sample, as long as the sample contains or may contain a second specific binding pair member. For example, the sample can be suspected of containing a protein that has an epitope recognized by an antibody included as the first specific binding pair member. The biological sample can be a tissue sample which contains, for example, 1 to 10,000,000; 1000 to 10,000,000; or 1,000,000 to 10,000,000 somatic cells. The sample need not contain intact cells, as long as it contains sufficient quantity of a specific binding pair member for the methods provided. According to aspects of the methods provided herein, wherein the biological sample is from a mammalian subject, the biological or tissue sample can be from any tissue. For example, the tissue can be obtained by surgery, biopsy, swab, stool, or other collection method. In other aspects, the biological sample contains, or is suspected to contain, or at risk for containing, a pathogen, for example a virus or a bacterial pathogen.

The term "binds specifically" or "specific binding activity," when used in reference to an antibody means that an interaction of the antibody and a particular epitope has a dissociation constant of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less. As such, Fab, F(ab')$_2$, Fd and Fv fragments of an antibody that retain specific binding activity, are included within the definition of an antibody.

As used herein, the term "specific binding pair member" refers to a molecule that specifically binds or selectively hybridizes to, or interacts with, another member of a specific binding pair. Specific binding pair members include, for example, analytes and biomolecules.

A "biomolecule" is a specific binding pair member found in nature, or derived from a molecule found in nature. Biomolecules can include, for example, biomolecules that have a molecular weight of at least 1 kDa, 2 kDa, 3, kDa, 4, kDa, 5 kDa, 10 kDa, 15 kDa, 20 kDa, 25 kDa, 50 kDa, or 100 kDa. Biomolecules include, for example, nucleic acid molecules, peptides, polypeptides, proteins, ligands, lipids, carbohydrates, or polysaccharides, but do not include water.

As used herein, the terms "analyte" refer to any atom, chemical, molecule, compound, composition or aggregate of interest for detection and/or identification. Non-limiting examples of analytes include an amino acid, peptide, polypeptide, protein, glycoprotein, lipoprotein, nucleoside, nucleotide, oligonucleotide, nucleic acid, sugar, carbohydrate, oligosaccharide, polysaccharide, fatty acid, lipid, hormone, metabolite, cytokine, chemokine, receptor, neurotransmitter, antigen, allergen, antibody, substrate, metabolite, cofactor, inhibitor, drug, pharmaceutical, nutrient, prion, toxin, poison, explosive, pesticide, chemical warfare agent, biohazardous agent, radioisotope, vitamin, heterocyclic aromatic compound, carcinogen, mutagen, narcotic, amphetamine, barbiturate, hallucinogen, waste product, virus, bacteria, protozoa, and/or contaminant.

As used herein, the term "antibody" is used in its broadest sense to include polyclonal and monoclonal antibodies. The term antibody as used herein is meant to include intact molecules as well as fragments thereof, such as Fab and $F(ab')_2$, Fv and SCA fragments which are capable of binding an epitopic determinant.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An $(Fab')_2$ fragment of an antibody can be obtained by treating a whole antibody molecule with the enzyme pepsin, without subsequent reduction. A $(Fab')_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281 (1989). These and other methods of making, for example, chimeric, humanized, CDR-grafted, single chain, and bifunctional antibodies are well known to those skilled in the art (Winter and Harris, *Immunol. Today* 14:243-246, 1993; Ward et al., *Nature* 341: 544-546, 1989; Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering*, 2d ed. (Oxford University Press 1995.

Methods for raising polyclonal antibodies, for example, in a rabbit, goat, mouse or other mammal, are well known in the art (see, for example, Green et al., "Production of Polyclonal Antisera," in *Immunochemical Protocols* (Manson, ed., Humana Press 1992), pages 1-5; Coligan et al., "Production of Polyclonal Antisera in Rabbits, Rats, Mice and Hamsters," in *Curr. Protocols Immunol.* (1992), section 2.4.1). In addition, monoclonal antibodies can be obtained using methods that are well known and routine in the art (Harlow and Lane, supra, 1988).

As used in this invention, the term "epitope" refers to an antigenic determinant on an antigen, to which the paratope of an antibody, binds. Antigenic determinants usually consist of chemically active surface groupings of molecules, such as amino acids or sugar side chains, and can have specific three-dimensional structural characteristics, as well as specific charge characteristics.

Examples of types of immunoassays of the invention include competitive and non-competitive immunoassays in either a direct or indirect format. Those of skill in the art will know, or can readily discern, other immunoassay formats without undue experimentation.

In performing a method of the present invention, "blocking agents" can be included in the incubation medium. "Blocking agents" are added to minimize non-specific binding to a surface and between molecules.

A "biomolecular binding event" or "biomolecular interaction" is a specific binding of specific binding pair members, wherein at least one of the specific binding pair members is a biomolecule. Methods provided herein can be used to detect molecular interaction (i.e. binding) of virtually any biomolecule with another molecule. For example, the methods can detect interaction of an analyte and a biomolecule.

The term "receptor" is used to mean a protein, or fragment thereof, or group of associated proteins that selectively bind a specific substance called a ligand. Upon binding its ligand, the receptor triggers a specific response in a cell.

The term "polypeptide" is used broadly herein to mean two or more amino acids linked by a peptide bond. The term "fragment" or "proteolytic fragment" also is used herein to refer to a product that can be produced by a proteolytic reaction on a polypeptide, i.e., a peptide produced upon cleavage of a peptide bond in the polypeptide. A polypeptide of the invention contains at least about six amino acids, usually contains about ten amino acids, and can contain fifteen or more amino acids, particularly twenty or more amino acids. It should be recognized that the term "polypeptide" is not used herein to suggest a particular size or number of amino acids comprising the molecule, and that a peptide of the invention can contain up to several amino acid residues or more. A protein is a polypeptide that includes other chemical moieties in addition to amino acids, such as phosphate groups or carbohydrate moieties.

The term "terahertz (i.e. THz) or gigahertz radiation" is radiation between the far infrared and high frequency RF ranges. For example, terahertz radiation can have a bandwidth spanning the range of 0.1 to 100 THz, which corresponds to about 3 millimeters to 3 micrometers in wavelength. The pulse of the terahertz radiation is typically short, and can be in the order of $10^{-12}$ seconds, which therefore has a relatively high peak power, and a short time resolution.

An "input radiation," as used herein, is the radiation coming from the radiation source before impingement on the sample. An "exit radiation" is the radiation traveling to the detector after being scattered or reflected by the sample.

In certain embodiments, a method to detect a biomolecule, that includes impinging the biomolecule with gigahertz or terahertz input radiation, and detecting an exit radiation, is provided. A shift in vibrational frequency of the exit radiation or a change in intensity level of the exit radiation compared to exit radiation detected from a control sample not comprising the biomolecule, is indicative of the presence of the biomolecule. In certain aspects, the exit radiation is detected by Raman spectroscopy. In other aspects, absorbance is detected by detecting a decrease in intensity level of the exit radiation. In certain examples, the biomolecule is isolated and optionally immobilized, before it is impinged with the input radiation.

The method for detecting a biomolecule using gigahertz or terahertz radiation can be used to detect a biomolecular interaction, also referred to herein as a biomolecular binding event. Accordingly, in another embodiment, provided herein is a method to detect a biomolecular interaction, including: contacting a first molecule with a second molecule, wherein the first molecule is a biomolecule that is suspected of binding to the second molecule; and impinging the first molecule with gigahertz or terahertz input radiation; and detecting an exit radiation. A shift in vibrational frequency or a change in intensity level of the exit radiation compared to exit radiation detected from a first molecule not bound to the second molecule, is indicative of a biomolecular interaction.

FIG. 1 shows one embodiment of the system 5, whereby terahertz radiation from radiation source 112 impinges upon a population of immobilized first molecules 20. An arrow 10 indicates the direction in which the input gigahertz or terahertz radiation travels, toward the immobilized biomolecules 20. The immobilized biomolecules 20 are attached to a substrate 22 and immersed in a reaction solution 24. In certain examples, the input radiation 10 from radiation source 112 has a bandwidth of between 0.001 and 1000 terahertz, for example between 0.01 and 100 terahertz, or between 0.1 and 10 terahertz.

After the first molecule 20 is impinged by the input radiation 10, exit radiation 30 is generated and travels toward a terahertz detector 116, which detects the exit radiation 30. The detected radiation is analyzed by a processor 118 for any changes in the vibrational spectrum or changes in intensity levels. When the immobilized biomolecules 20 experience a binding event with free molecules in the solution 24, the exit radiation demonstrates a frequency shift in the vibrational spectrum and/or an energy absorption compared to the vibrational spectrum or energy absorption of the immobilized biomolecules 20 when they are not bound to the second molecule. Thus, a change in the vibrational spectra and/or an occurrence of absorption, that is different from that observed or expected for unbound immobilized biomolecules 20, indicates that the immobilized molecules 20 and the free molecules bind. For example, a 0.001, 0.002, 0.003, 0.004, 0.005, 0.01, 0.02, 0.03, 0.04, 0.05, 0.1, 0.2, 0.3, 0.4, 0.5, 1, 2, 3, 4, 5, 10, 15, 20, 25, 30, 40, and 50% reduction in intensity level can be indicative of the occurrence of a biomolecular binding event. In another example, the frequency shift of 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 10, 20, 30, 40, 50, 60, 70, 80, 90, and 100 THz can be indicative of occurrence of a biomolecular binding event. Vibration spectra can be generated and recorded for a first molecule not bound to a second molecule, and used to compare to vibration spectra in the presence of a sample suspected of containing the second molecule.

Figure 2:
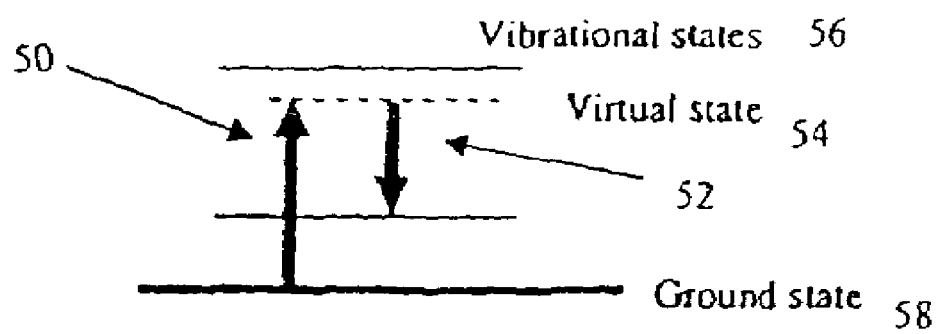
FIG. 2 is a diagram showing frequency transition in Raman spectroscopy caused by terahertz radiation.
Figure 3:
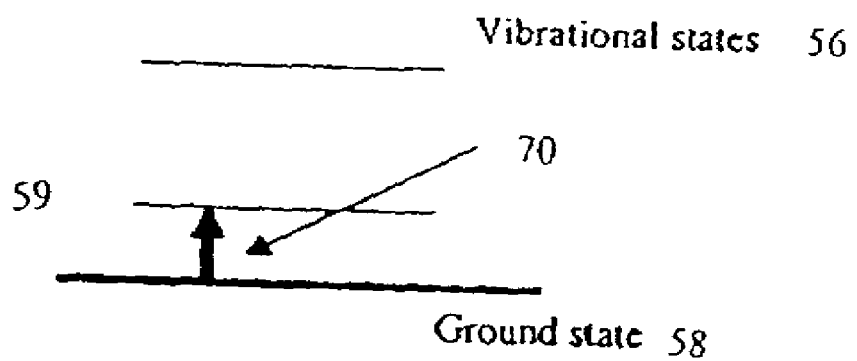
FIG. 3 is a diagram showing energy absorption caused by terahertz radiation.
Figure 5:
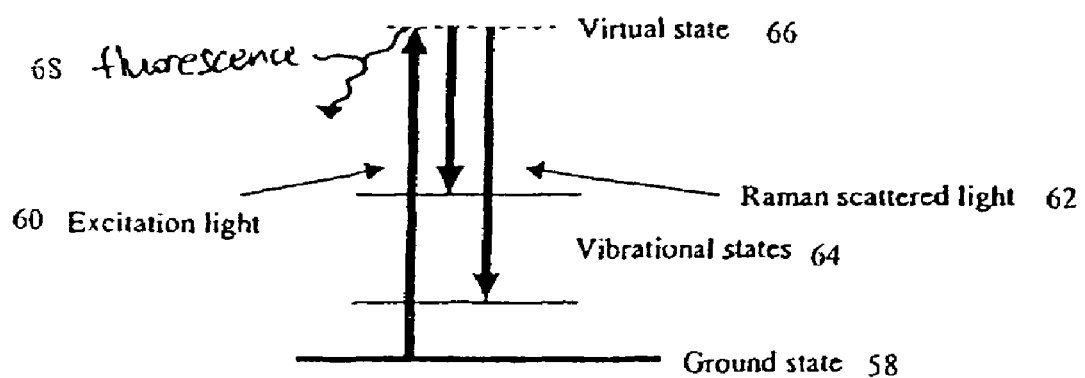
FIG. 5 is a diagram showing a frequency transition in Raman spectroscopy using ultraviolet/visible/near-infrared radiation to excite a nucleic acid.
Figure 6:
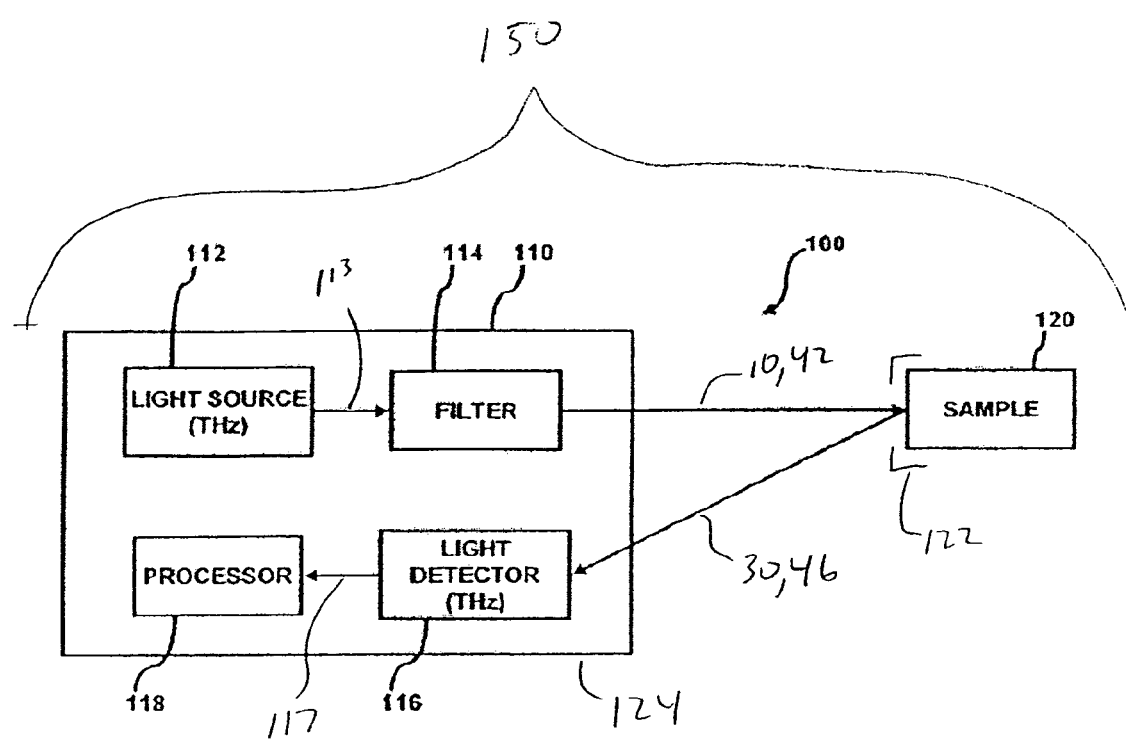
FIG. 6 is a block diagram of one embodiment of an apparatus for detecting a bimolecular binding event.

As illustrated in FIG. 5, excitation of a biomolecule caused by ultraviolet/visible/near-infrared radiation 60, excites the biomolecule to a virtual state 65 and results in the generation of Raman scattered light 62, but also excites the biomolecule from a ground state 58 to an unnecessary electronic excited state 66 resulting in fluorescence 68. FIG. 2 is a diagram showing the molecular energy state transition caused by terahertz radiation 50, which due to its low energy level excites the biomolecule to lower and more desirable virtual states 54 and vibrational states 56 while generating Raman scattered light 52. By keeping the excitation level low, fluorescence 68 is avoided. Since fluorescence 68 is responsible for background noise in the signal, use of terahertz radiation results in a signal with reduced background emissions. Vibrational frequency shift produced as a result of impingement of a biomolecule with gigahertz or terahertz radiation can be detected using Raman spectroscopy. FIG. 3 provides a diagram showing the molecular energy state caused by biomolecule's absorption 70 of terahertz radiation. Energy of the terahertz radiation is absorbed 70 when the energy level of the terahertz radiation matches the energy level of the vibrational state 59.

In illustrative examples, absorbance is detected by detecting a decrease in the intensity level of exit radiation compared to the intensity level of the corresponding input radiation. In examples where a decrease in intensity level is detected, the gigahertz or terahertz radiation can include a target wavelength, or range of wavelengths, known to be absorbed by the first molecule, and/or by a complex that includes a first molecule bound to a second molecule. It will be understood that wavelength scanning can be performed to identify wavelengths that are absorbed by the first molecule to identify a target wavelength or target range of wavelengths. Furthermore, scanning can be performed of various emission energy levels to identify a vibrational level, below which Raman transmissions are minimized. In an alternative embodiment, a broad band terahertz light source can be used in conjunction with a spectrum analyzer or a similar device that can analyze the absorbance spectrum over a range of wavelengths.

In embodiments of the invention directed to detecting biomolecular interactions, a second molecule known to bind, or suspected of binding to the first molecule, is found in the reaction solution 24, where it contacts the immobilized first molecules 20. Alternatively, the reaction solution can include a biological sample suspected of containing the second molecule, which can be an analyte. Accordingly, in another embodiment, a method is provided to detect an analyte in a biological sample, including: contacting the biological sample with a first molecule immobilized on a substrate, wherein the first molecule binds to, or is suspected of binding to the analyte; impinging the first molecule with a gigahertz or terahertz input radiation; and detecting a vibrational spectrum of the first molecule. A shift in the vibrational spectrum, or decrease in an intensity level of the vibrational spectrum, compared to a vibrational spectrum of a first molecule not associated with the analyte, is indicative of the presence of the analyte in the sample.

Due to the known water absorption property of terahertz radiation, in one embodiment of the invention, the radiation source may be arranged so that the input radiation strikes the immobilized molecules 20 from the substrate side, where the radiation travels through the substrate, and therefore travels through minimum solution depth to reach the immobilized molecules 20. Therefore, in certain illustrative examples, the gigahertz or terahertz radiation impinges the first molecule 20 through the substrate. The radiation, upon striking the immobilized molecules 20, is reflected or scattered in the direction indicated by an arrow 30.

Suitable conditions for performing a method of the invention include any conditions that allow a first molecule to specifically interact with a second molecule. An advantage of the present invention is that it allows terahertz radiation to be used to detect biomolecular binding events in aqueous (i.e. water-containing) samples. Therefore, the conditions, such as temperature, and reaction solution composition, can be those typically used for the type of biomolecular binding being analyzed. For example, in examples where the method is used to detect binding of an antibody to an analyte (i.e. an immunoassay) typical immunoassay conditions can be used.

In embodiments where nucleic acid hybridization is detected, conditions for hybridization reactions well known in the art, can be used. For example, hybridization of a first nucleic acid molecule with a second nucleic acid molecule can be performed under moderately stringent or highly stringent physiological conditions, as are known in the art. An example of progressively higher stringency conditions that can be used in the methods disclosed herein are as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, for example, high stringency conditions, or each of the conditions can be used, for example, for 10 to 15 minutes each, in the order listed above, repeating any or all of the steps listed.

Certain illustrative embodiments of the invention are provided herein in the context of using terahertz radiation to detect nucleic acid hybridization. However, it will be understood that the embodiments provided herein are illustrative embodiments, and the scope of the invention is not limited to the applications or the embodiments disclosed herein.

The methods disclosed herein can be used to detect virtually any biomolecular binding event that demonstrates a frequency shift in the vibrational spectrum. The biomolecular binding event typically involves specific binding of a first and second specific binding pair member, wherein at least one of the specific binding pair members is a biomolecule. As indicated herein, the first specific binding pair member is typically a biomolecular with a molecular weight of at least 1 kDa. In addition to nucleic acids, the biomolecules also include, for example, a receptor and a ligand, or an antigen and an antibody. In one aspect, the first molecule is a protein, such as an antibody molecule, or fragment thereof, and the second molecule is a protein, that includes an epitope recognized by the antibody. In another example, the first molecule is a receptor and the second molecule is a ligand. In an illustrative aspect, the first or second molecule is a nucleic acid molecule that interacts with another molecule. Accordingly, this embodiment can be used to detect binding of nucleic acid molecules to a protein, or binding of a protein to a nucleic acid molecule.

The use of first and second molecules is illustrative. However, there can be additional molecules. For example, a third molecule that binds to the first molecule can be included. Binding of the second molecule can displace the third molecule in a competitive manner and, as a result, shift the vibrational frequency or change the intensity level of the exit radiation.

Accordingly, the immobilized biomolecules 20 can be any biomolecule capable of forming a specific binding pair with another molecule. The immobilized biomolecule can be, for example, a nucleic acid, protein, antigen, antibody, receptor, or ligand. The reaction solution 24 contains free molecules that may or may not bind to the immobilized biomolecules 20. Therefore, the invention can be used to determine whether binding, such as a nucleic acid hybridization, has occurred by detecting a shift in vibrational frequency or a change in intensity level of exit radiation.

As an illustrative example, such as shown in FIG. 1, nucleic acid hybridization can be detected using the methods provided herein. If a single stranded nucleic acid with the nucleotide sequence GGCAAT is immobilized on a substrate 22 and incubated under highly stringent conditions with a nucleic acid sample, the vibrational spectrum of the GGCAAT nucleic acid molecule after irradiation with terahertz radiation will be affected if the nucleic acid sample includes a nucleic acid that binds to GGCAAT under highly stringent hybridization conditions. Therefore, the vibrational spectrum of the GGCAAT nucleic acid molecule after irradiation with terahertz radiation will be different if the nucleic acid sample includes a nucleic acid molecule that hybridizes to GGCAAT, as compared to the vibrational spectrum generated for the nucleic acid molecule GGCAAT in the absence of a hybridizing nucleic acid molecule. This difference indicates that the nucleic acid sample includes a nucleic acid molecule that hybridizes with GGCAAT, such as a nucleic acid molecule that has the sequence CCGTTA. As indicated in this example, DNA hybridization typically results in changes in fundamental vibrational and rotational modes. As another example, the methods disclosed herein can be used to detect analytes, such as protein analytes, in a sample. For example, if the immobilized molecule 20 is an antibody, a change in the vibrational spectrum indicates that the reaction solution 24, which in this example can be a patient serum sample, contains a protein that is recognized by the immobilized antibody. It will understand that the invention is useful for detecting other types of binding events as well, provided that they involve a biomolecule and result in a shift in the vibrational spectrum or a change in the intensity level of the exit radiation upon binding.

Since the radiation travels through the substrate 22, the substrate 22 is preferably made of a material (e.g., glass) that is transparent to the radiation being used. As long as the substrate 22 is transparent to the radiation, there is no restriction on its thickness.

Immobilized biomolecules according to the present invention, can be immobilized as a single population of identical biomolecules, or as an array or a desired pattern of immobilized populations of biomolecules. These arrays can be immobilized, for example, on biochips, as discussed in more detail herein.

Immobilized arrays of nucleic acid molecules can be used, for example, in determining nucleotide sequence information using sequencing by hybridization reactions. In sequencing by hybridization reactions, one or more oligonucleotide probes of known sequence are allowed to hybridize to a target nucleic acid sequence. Binding of the labeled oligonucleotide to the target indicates the presence of a complementary sequence in the target strand. Multiple labeled probes can be allowed to hybridize simultaneously to the target molecule and detected simultaneously. In alternative embodiments, bound probes can be identified attached to individual target molecules, or alternatively multiple copies of a specific target molecule can be allowed to bind simultaneously to overlapping sets of probe sequences. Individual molecules or a subpopulation thereof, can be scanned, for example, using known molecular combing techniques coupled to a detection method disclosed herein.

Regarding the reaction solution 24, it is preferred that the depth of the reaction solution 24 is not much greater than 100, 50, 40, 30, 25, or 20 microns in aspects where the radiation source transmits radiation though the reaction solution to impinge the first molecule. Thirty microns is the approximate penetration limit of terahertz radiation in water. As each nucleotide base has a length of approximately 0.3 nm, most samples will be immersed in a 30-micron-deep solution for terahertz spectroscopy. Any well-known method may be used for binding the immobilized molecules 20 to a substrate 22.

Figure 4:
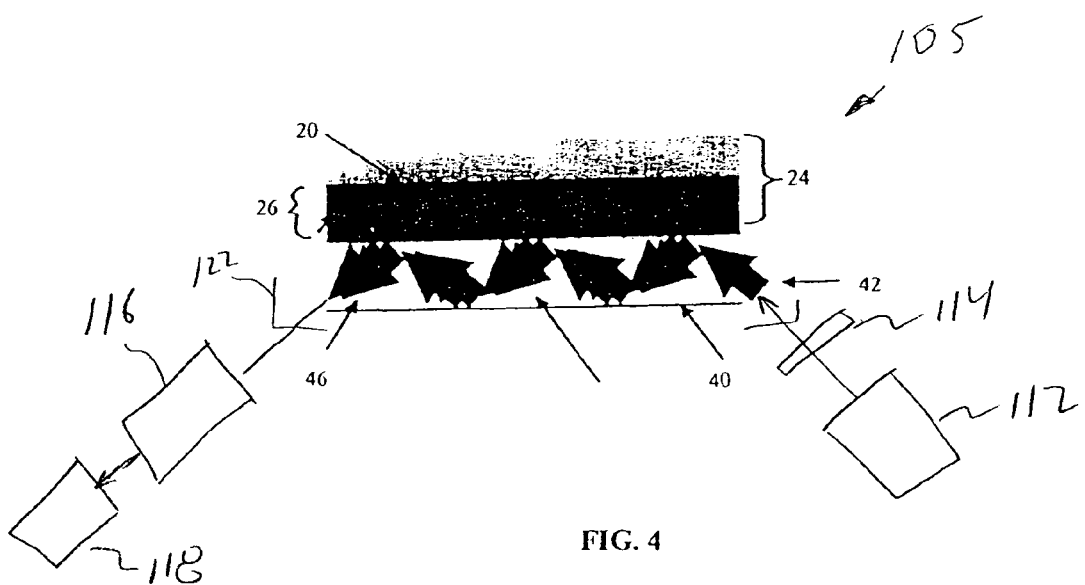
FIG. 4 is an illustration of another embodiment of a system whereby total internal reflection geometry is used to deliver excitation radiation 42 and to collect Raman scattered radiation 46.

FIG. 4 is an illustration of an embodiment of the invention whereby terahertz radiation impinges upon an immobilized population of first molecules 20, such as an immobilized population of nucleic acid molecules, and whereby a waveguide 40 is used to confine input radiation to create an excitation range 26 which includes the immobilized nucleic acid molecules 20. As disclosed above in reference to FIG. 1, the immobilized molecules 20 are immersed in a reaction solution 24. Unlike the first embodiment shown in FIG. 1, however, the immobilized biomolecules 20 are attached to a waveguide 40 through which radiation travels. Since the input radiation enters the waveguide 40 in a substantially orthogonal manner with respect to the substrate, from the direction indicated by the arrow 42, the solution 24 is not limited in depth. For example, input radiation can enter the waveguide at a 5, 10, 20, 30, 40, 45, 50, 60, 70, 75, 80, or 85° angle with respect to the waveguide 40. The waveguide 40 is typically made of a material that has a high index of refraction at the wavelength of the radiation being used, thereby keeping a vast majority of the radiation traveling through within the waveguide by total internal reflection. The exit radiation coming out of the waveguide 40 includes at least one of the Raman scattered radiation and the totally internally reflected radiation minus any absorption. As the radiation travels through the waveguide 40, it creates an excitation region 26 in the solution 24. The excitation region is typically between 10 and 100 um in depth.

In certain aspects, where binding of two nucleic acid molecules with similar length is to be detected, their rotational bands may appear very close to each other. By labeling one of the nucleic acid molecules, the rotational bands can be shifted to obtain different binding signatures. Non-limiting examples of labels that can be used include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins and aminoacridine. Polycyclic aromatic compounds in general can function as Raman labels, as is known in the art. These and other labels can be obtained from commercial sources (e.g., Molecular Probes, Eugene, Oreg.). Other labels that can be of use include cyanide, thiol, chlorine, bromine, methyl, phosphorus and sulfur. Carbon nanotubes can also be of use as labels.

Labels can be attached directly to the specific binding pair members or can be attached via various linker compounds. Raman labels that contain reactive groups designed to covalently react with other molecules, are commercially available (e.g., Molecular Probes, Eugene, Oreg.).

Figure 7:
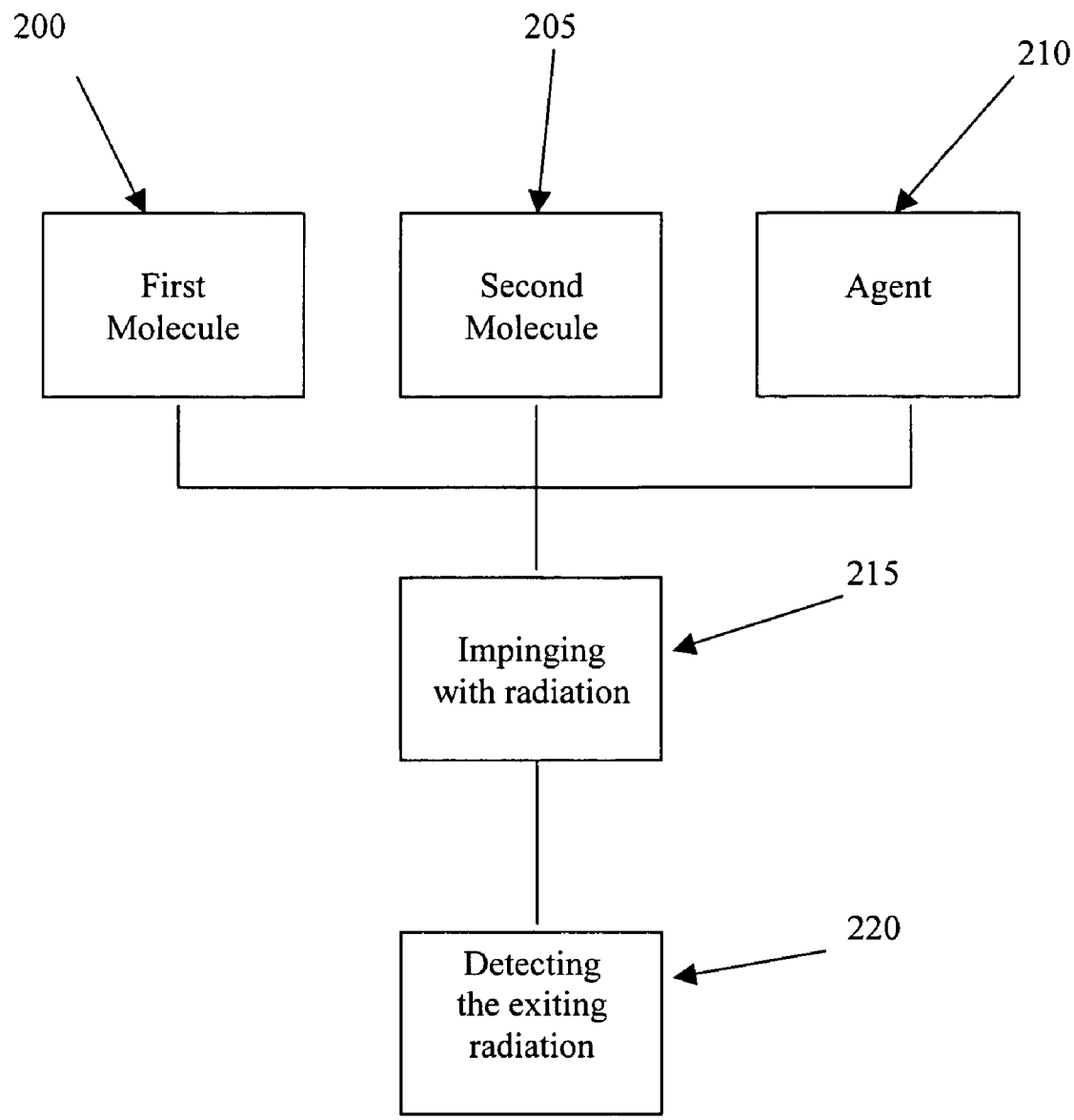
FIG. 7 is a block diagram of one embodiment of a method to identify an agent that affects a biomolecular binding.

In another embodiment illustrated in FIG. 7, provided herein is a method to identify an agent that affects a biomolecular binding, including: contacting under suitable conditions, a first molecule 200, a second molecule 205, and the agent 210, wherein the first molecule binds to, or is suspected of binding to, the second molecule, and wherein the first molecule is immobilized on a support. The first molecule is then impinged with a gigahertz or terahertz light source 215; and a vibrational spectrum of the first molecule is detected 220, wherein a shift in the vibrational spectrum or a change in intensity level of the vibrational spectrum, compared to a vibrational spectrum of a first molecule bound to the second molecule in the absence of the agent, identifies the agent as an agent that affects the biomolecule binding.

The first molecule, the second molecule, and the agent can be contacted in any order as desired. As such, the screening method can be used to identify agents that can competitively or non competitively inhibit binding of the first molecule to the second molecule, agents that can mediate or enhance binding of the first molecule to the second molecule, and agents that can induce dissociation of specifically bound first molecule from specific bound second molecule. Appropriate control reactions are performed to confirm that the action of the agent is specific with respect to the first molecule and the second molecule.

A screening method of the invention also can be performed using molecular modeling to identify candidate agents. The utilization of a molecular modeling method provides a convenient, cost effective means to identify those agents, among a large population such as a combinatorial library of potential agents, that are most likely to interact specifically with a biomolecule, thereby reducing the number of potential agents that need to be screened using an assay.

The term "test agent" or "test molecule" is used broadly herein to mean any agent that is being examined for agonist or antagonist activity in a method of the invention. Although the method generally is used as a screening assay to identify previously unknown molecules that can act as agonist or antagonist agents as described herein, the methods also can be used to confirm that a agent known to have a particular activity in fact has the activity, for example, in standardizing the activity of the agent.

A screening method of the invention provides the advantage that it can be adapted to high throughput analysis and, therefore, can be used to screen combinatorial libraries of test agents in order to identify those agents that can modulate binding of the first molecule to the second molecule. Methods for preparing a combinatorial library of molecules that can be tested for a desired activity are well known in the art and include, for example, methods of making a phage display library of peptides, which can be constrained peptides (see, for example, U.S. Pat. No. 5,622,699; U.S. Pat. No. 5,206, 347; Scott and Smith, Science 249:386-390, 1992; Markland et al., Gene 109:13 19, 1991; each of which is incorporated herein by reference); a peptide library (U.S. Pat. No. 5,264, 563, which is incorporated herein by reference); a peptidomimetic library (Blondelle et al., Trends Anal. Chem. 14:83 92, 1995; a nucleic acid library (O=Connell et al., supra, 1996; Tuerk and Gold, supra, 1990; Gold et al., supra, 1995; each of which is incorporated herein by reference); an oligosaccharide library (York et al., Carb. Res., 285:99 128, 1996; Liang et al., Science, 274:1520 1522, 1996; Ding et al., Adv. Expt. Med. Biol., 376:261 269, 1995; each of which is incorporated herein by reference); a lipoprotein library (de Kruif et al., FEBS Lett., 399:232 236, 1996, which is incorporated herein by reference); a glycoprotein or glycolipid library (Karaoglu et al., J. Cell Biol., 130:567 577, 1995, which is incorporated herein by reference); or a chemical library containing, for example, drugs or other pharmaceutical agents (Gordon et al., J. Med. Chem., 37:1385-1401, 1994; Ecker and Crooke, Bio/Technology, 13:351-360, 1995; each of which is incorporated herein by reference).

In another embodiment, a terahertz/gigahertz detection unit apparatus 100 for detecting a biomolecular binding event is provided. The apparatus 100 includes a terahertz light source or terahertz radiation source 112 positioned to aim an input radiation 10, 42 toward the sample 120 and a detector 116 for receiving an exit radiation 30, 46 reflecting from the sample 120. A processor 118 is also provided to receive the data 117 from the detector 116 and analyze the data. In some embodiments, the light source 112, detector 116 and processor 118 are located in a housing 124. A filter 114 may also be positioned between the light source 112 and the sample 120 to select a predetermined bandwidth of the beam of light 113 emitted by the light source. An optional sample holder 122 may also be provided to position and/or hold the sample 120 in the proper position during testing. In some embodiments, the substrate may be part of the sample holder. In other embodiments, the waveguide may be part of the sample holder. In still other embodiments, the sample holder secures the sample at a preferred distance and/or orientation from the light source and detector. In other embodiments, the light source and/or the detector capable of being rotated, oriented or adjusted to a preferred orientation.

In another embodiment, provided herein is a system 150 for detecting a biomolecular binding event, including a sample 120 containing a first molecule and a second molecule, wherein the first molecule binds to, or is suspected of binding to the second molecule; a terahertz or gigahertz radiation source 112 positioned to aim an input radiation 10, 42 toward the sample 120; and a detector 116 for receiving an exit radiation 30, 46 reflecting from the sample. In certain illustrative examples, the system 150 further includes a substrate 22 that is transparent to the terahertz or gigahertz radiation, wherein the first molecule is immobilized on the substrate 22.

The system typically includes a reaction chamber adjacent to the substrate for containing at least one of the biomolecules and the reaction solution. The reaction solution can be an organic solution, but is typically an aqueous solution, which therefore contains water. The system can also include a waveguide 40, as illustrated in FIG. 4. The substrate 22 can be a surface of a waveguide 40. The system can also include diffraction gratings, but typically includes at most one diffraction grating positioned between the sample and the detector.

Systems 150 of the present invention typically include a terahertz/gigahertz detection unit 100. The terahertz/gigahertz detection unit 100 includes a terahertz and/or gigahertz radiation source 112 and a detector 116, which can be wavelength-selective detector. The excitation source 112 illuminates an immobilized biomolecule, and optionally a second molecule associated with the first molecule, in a sample 120 with an excitation beam 10, 42. The excitation beam 10, 42 interacts with the first molecule, resulting in the excitation of electrons to a higher energy state. As the electrons return to a lower energy state, they emit a Raman emission signal that is detected by the Raman detector. In other embodiments, as discussed herein, absorbance of the gigahertz and/or terahertz radiation by the first molecule is detected. Virtually any type of terahertz and/or gigahertz source can be used to generate terahertz and/or gigahertz radiation for the systems 150, apparatus 100 and methods of the present invention. For example, terahertz radiation can be generated using a femtosecond laser that is directed into an electro-optic crystal such as a zinc blend crystal (e.g., zinc telluride crystal, gallium arsenide crystal). In another approach, a photoconductive dipole antenna can be used (Lai et al, App. Phys. Lett. 72:3100 (1998)). In another embodiment, terahertz radiation can be obtained by mixing multiple emissions from near-infrared diode lasers (NASA Jet Propulsion Laboratory, Pasadena, Calif. reported in NASA TechBriefs, October, 2000). Furthermore, a terahertz or gigahertz transistor, such as the transistors used in a computer processor, for example a Pentium® processor can be used.

Detectors for detecting radiation in the terahertz/gigahertz frequency range are known (See e.g., J. Applied Phys. 93, 1897 (2003)). In another approach, nanometer size objects (e.g. quantum dots, nanowires, and nano channels) can be used to detect terahertz/gigzhertz radiation (Xing and Liu, Semicon. Sci. Technol. 10:1139 (1995)). Furthermore, the detection of reflected terahertz radiation can be achieved by using a electro-optic crystal and by using a photodiode. In this aspect, the detector may include an electro-optic crystal which in response to terahertz radiation alters its optical characteristics such that laser radiation directed upon the photodiode reveals the terahertz radiation. The optical characteristic can include the polarization experienced by laser radiation passing through the crystal.

Data can be collected from a detector 116 and provided to an information processing and control system 118. The information processing and control system 118 can perform standard procedures known in the art, such as subtraction of background signals. Furthermore, the information processing and control system 118 can analyze the data to determine nucleotide sequence information from detected signals and the temporal relationship of these signals.

As indicated above, in certain aspects of the invention, the first molecule is immobilized on an immobilization substrate. The type of substrate to be used for immobilization of the first molecule is not limiting as long as it is effective for immobilizing a first molecule while providing access of the first molecule to the second molecule and, in certain examples, allowing terahertz and/or gigahertz radiation to pass through. In illustrative examples, the substrate is transparent. Non-limiting examples of surfaces that can be used include glass, silicon, germanium, gallium arsenide, silica, silicate, silicon oxinitride, nitrocellulose, nylon, activated quartz, activated glass, polyvinylidene difluoride (PVDF), polystyrene, polyacrylamide, other polymers such as poly(vinyl chloride), poly (methyl methacrylate) or poly(dimethyl siloxane), and photopolymers which contain photoreactive species such as nitrenes, carbenes and ketyl radicals. Various methods of attaching specific binding pair members to surfaces are known in the art and can be employed. For example cross-linking agents can be used. Furthermore, functional groups can be covalently attached to cross-linking agents so that binding interactions between biomolecules can occur without steric hindrance. Typical cross-linking groups include ethylene glycol oligomers and diamines. Attachment can be by either covalent or non-covalent binding. The cross-linking groups for attaching biomolecules to immobilization surfaces are referred to herein as immobilization groups.

As another specific example, immobilization can be achieved by coating a surface with streptavidin or avidin and the subsequent attachment of a biotinylated first molecule, such as a biotinylated antibody (See Holmstrom et al., *Anal. Biochem.* 209:278-283, 1993 for method using nucleic acids). Immobilization can also involve coating a silicon, glass or other surface with poly-L-Lys (lysine). Amine residues can be introduced onto a surface through the use of aminosilane for cross-linking.

The first molecule can be bound to glass by first silanizing the glass surface, then activating with carbodiimide or glutaraldehyde. Alternative procedures can use reagents such as 3-glycidoxypropyltrimethoxysilane (GOP) or aminopropyltrimethoxysilane (APTS). Certain specific binding pair members can be bound directly to membrane surfaces using ultraviolet radiation.

Bifunctional cross-linking reagents can be of use for attaching a biomolecule to a surface. The bifunctional cross-linking reagents can be divided according to the specificity of their functional groups, e.g., amino, guanidino, indole, or carboxyl specific groups. Of these, reagents directed to free amino groups are popular because of their commercial availability, ease of synthesis and the mild reaction conditions under which they can be applied. Exemplary methods for cross-linking molecules are disclosed in U.S. Pat. Nos. 5,603, 872 and 5,401,511. Cross-linking reagents include glutaraldehyde (GAD), bifunctional oxirane (OXR), ethylene glycol diglycidyl ether (EGDE), and carbodiimides, such as 1-ethyl-3-(3-dimethylaminopropyl)carbodiimide (EDC).

In some embodiments of the invention, a method disclosed herein can be performed in a micro-electro-mechanical system (MEMS) 300, illustrated in FIG. 7. MEMS 300 are integrated systems that include mechanical elements, sensors, actuators, and electronics. All of those components can be manufactured by known microfabrication techniques on a common chip, including a silicon-based or equivalent substrate (e.g., Voldman et al., *Ann. Rev. Biomed. Eng.* 1:401-425, 1999). The sensor components of MEMS can be used to measure mechanical, thermal, biological, chemical, optical and/or magnetic phenomena. The electronics can process the information from the sensors and control actuator components such pumps, valves, heaters, coolers, filters, etc. thereby controlling the function of the MEMS.

The electronic components of MEMS can be fabricated using integrated circuit (IC) processes (e.g., CMOS, Bipolar, or BICMOS processes). They can be patterned using photolithographic and etching methods known for computer chip manufacture. The micromechanical components can be fabricated using compatible "micromachining" processes that selectively etch away parts of the silicon wafer or add new structural layers to form the mechanical and/or electromechanical components.

Basic techniques in MEMS manufacture include depositing thin films of material on a substrate, applying a patterned mask on top of the films by photolithographic imaging or other known lithographic methods, and selectively etching the films. A thin film can have a thickness in the range of a few nanometers to 100 micrometers. Deposition techniques of use may include chemical procedures such as chemical vapor deposition (CVD), electrodeposition, epitaxy and thermal oxidation and physical procedures like physical vapor deposition (PVD) and casting.

Figure 8:
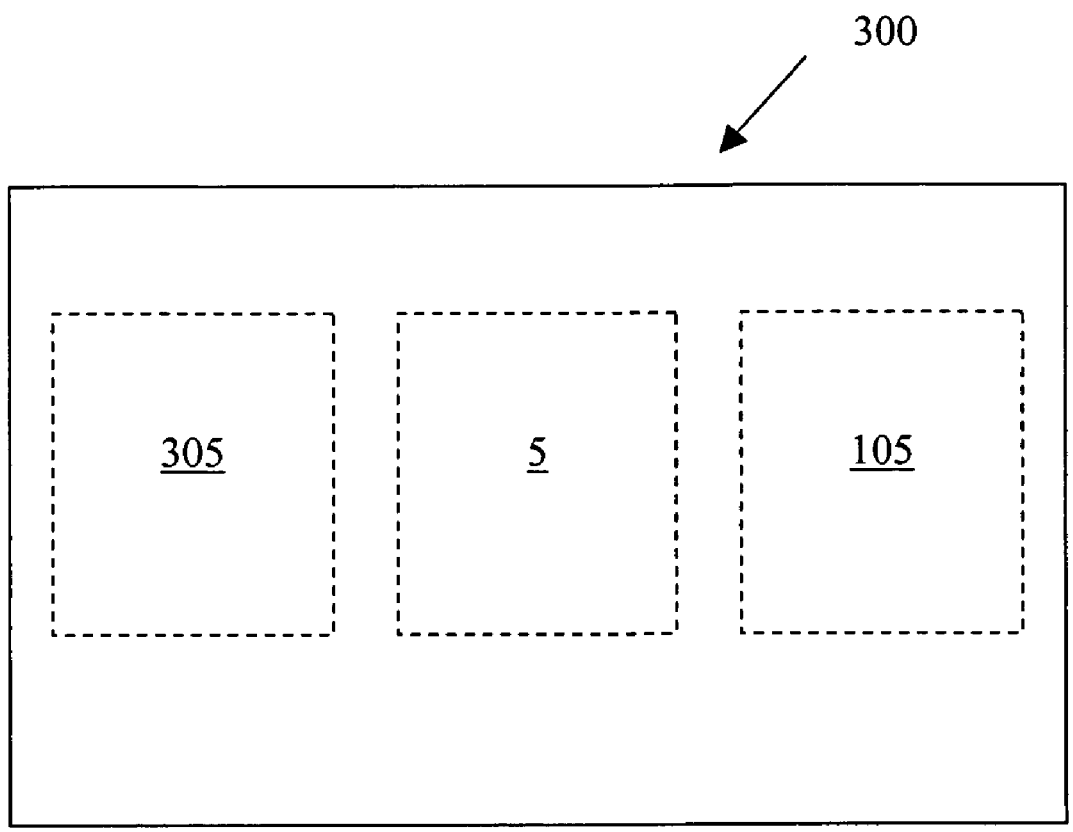
FIG. 8 is an illustration of an embodiment of a micro-electro-mechanical system (MEMS) that incorporates may incorporate the systems illustrated in FIGS. 1 and/or 4.

In some embodiments of the invention, MEMS devices 300 include various fluid filled compartments 305, such as microfluidic channels, nanochannels and/or microchannels. In one embodiment, systems 5 and 105 may be constructed as a MEMS device, as shown in FIG. 8. These and other components of the apparatus can formed as a single unit, for example in the form of a chip as known in semiconductor chips and/or microcapillary or microfluidic chips. Alternatively, an immobilization substrate, such as a metal coated porous silicon substrate, can be removed from a silicon wafer and attached to other components of an apparatus. Any materials known for use in such chips may be used in the disclosed apparatus, including silicon, silicon dioxide, silicon nitride, polydimethyl siloxane (PDMS), polymethylmethacrylate (PMMA), plastic, glass, quartz.

Techniques for batch fabrication of chips are well known in the fields of computer chip manufacture and/or microcapillary chip manufacture. Such chips may be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding with a flowable, optically clear material such as plastic or glass; photolithography and dry etching of silicon dioxide; electron beam lithography using polymethylmethacrylate resist to pattern an aluminum mask on a silicon dioxide substrate, followed by reactive ion etching. Known methods for manufacture of nanoelectromechanical systems may be used for certain embodiments of the invention. (See, e.g., Craighead, Science 290: 1532-36, 2000.) Various forms of microfabricated chips are commercially available from, e.g., Caliper Technologies Inc. (Mountain View, Calif.) and ACLARA BioSciences Inc. (Mountain View, Calif.).

In certain embodiments of the invention, part or all of the apparatus can be selected to be transparent to terahertz and/or gigahertz radiation, such as glass, silicon, quartz or any other optically clear material. For fluid-filled compartments that may be exposed to various biomolecules, such as proteins, peptides, nucleic acids, nucleotides and the like, the surfaces exposed to such molecules may be modified by coating, for example to transform a surface from a hydrophobic to a hydrophilic surface and/or to decrease adsorption of molecules to a surface. Surface modification of common chip materials such as glass, silicon, quartz and/or PDMS is known in the art (e.g., U.S. Pat. No. 6,263,286). Such modifications may include, but are not limited to, coating with commercially available capillary coatings (Supelco, Bellafonte, Pa.), silanes with various functional groups such as polyethyleneoxide or acrylamide, or any other coating known in the art.

Although the invention has been described with reference to the above examples, it will be understood that modifications and variations are encompassed within the spirit and scope of the invention. Accordingly, the invention is limited only by the following claims.

What is claimed is:

1. A method to detect a biomolecular interaction by a terahertz Raman spectroscopy, comprising:
   detecting an exit radiation from a first molecule not bound to a second molecule;
   contacting the first molecule with the second molecule in a fluid compartment, wherein the first molecule is a biomolecule suspected of binding to the second molecule;
   impinging the first molecule bound to the second molecule with gigahertz or terahertz input radiation from a radiation source; and
   detecting with a detector an exit radiation from the first molecule bound to the second molecule, wherein a shift in vibrational frequency of the exit radiation from the first molecule bound to the second molecule compared to the exit radiation detected from the first molecule not bound to the second molecule is determined with a processor and is indicative of the biomolecular interaction, wherein the first molecule is immobilized on a substrate; further wherein the gigahertz or terahertz radiation impinges the first molecule through the substrate and is reflected back from the first molecule through the substrate onto a detector,
   wherein the shift in vibrational frequency is detected by detecting using terahertz Raman spectroscopy and
   wherein the input radiation is directed through a waveguide positioned adjacent to the first molecule, by reflecting the input radiation off an inner wall of the waveguide, and
   wherein the fluid compartment, radiation source, detector, and the processor are formed as a single integrated unit on a chip.

2. The method of claim 1, wherein the first molecule is a nucleic acid.

3. The method of claim 2, wherein the second molecule is a nucleic acid.

4. The method of claim 3, wherein the first molecule and/or the second molecule is a human nucleic acid.

5. The method of claim 3, wherein the first molecule and/or the second molecule is a bacterial nucleic acid.

6. The method of claim 3, wherein the first molecule and/or the second molecule is a viral nucleic acid.

7. The method of claim 3, wherein the second molecule is a protein.

8. The method of claim 1, wherein the first molecule is a receptor and the second molecule is a ligand.

9. The method of claim 1, wherein the first molecule is a protein and the second molecule is a protein.

10. The method of claim 1, wherein a change in intensity level is detected between the exit radiation from the first molecule not bound to the second molecule and the exit radiation from the first molecule bound to the second molecule.

11. The method of claim 10, wherein the gigahertz or terahertz radiation comprises a target wavelength range known to be absorbed by the first molecule.

12. The method of claim 1, wherein the input radiation has a bandwidth of between 0.1 and 10 terahertz.

13. The method of claim 1, wherein the waveguide is made of a material with a high index of refraction for terahertz or gigahertz radiation.

14. The method of claim 1, wherein the fluid comprises water.

15. The method of claim 1, wherein the first and second molecules comprise specific binding pair.

16. The method of claim 1, wherein at least one of the first and second molecules comprises a label.

\* \* \* \* \*